(12) United States Patent
Hohmann et al.

(10) Patent No.: US 10,272,459 B2
(45) Date of Patent: Apr. 30, 2019

(54) CHILD-PROOF DISCHARGER

(71) Applicant: MeadWestvaco Calmar GmbH, Hemer (DE)

(72) Inventors: Thomas Hohmann, Hemer (DE); Gisbert Welp, Sundern (DE)

(73) Assignee: Silgan Dispensing Systems Hemer GmbH, Norcross, GA (US)

( * ) Notice: Subject to any disclaimer, the term of this patent is extended or adjusted under 35 U.S.C. 154(b) by 470 days.

(21) Appl. No.: 14/651,544

(22) PCT Filed: Dec. 17, 2013

(86) PCT No.: PCT/EP2013/003818
§ 371 (c)(1),
(2) Date: Jun. 11, 2015

(87) PCT Pub. No.: WO2014/095045
PCT Pub. Date: Jun. 26, 2014

(65) Prior Publication Data
US 2015/0328651 A1    Nov. 19, 2015

(30) Foreign Application Priority Data
Dec. 18, 2012  (DE) .................. 10 2012 024 681

(51) Int. Cl.
*B05B 11/00*    (2006.01)
*A61M 15/08*    (2006.01)
(Continued)

(52) U.S. Cl.
CPC ...... *B05B 11/0032* (2013.01); *B05B 11/3001* (2013.01); *B05B 11/3059* (2013.01);
(Continued)

(58) Field of Classification Search
CPC .......... A61M 15/08; A61M 2205/7518; A61M 11/006; A61M 39/162; A61M 39/20;
(Continued)

(56) References Cited

U.S. PATENT DOCUMENTS 4,440,207 A * 4/1984 Genatempo ............. A61L 31/16
                                                          150/154
4,773,567 A   9/1988 Stoody
(Continued)

FOREIGN PATENT DOCUMENTS

DE    69803036 T2    8/2002
DE    10134796 A1    1/2003
(Continued)

OTHER PUBLICATIONS

English translation of the International Preliminary Report on Patentability dated Jul. 16, 2015, corresponding to PCT/EP2013/003818.
(Continued)

*Primary Examiner* — Nathan R Price
*Assistant Examiner* — Justin L Zamory
(74) *Attorney, Agent, or Firm* — Barlow, Josephs & Holmes, Ltd.

(57) ABSTRACT

Child-proof discharger for media, comprising a reservoir (1), a pump part (3), mounted on the reservoir (1) in sealed arrangement via a closure element (2), for pumping medium out of the reservoir (1), an actuable discharge portion (4), which is mounted on the pump part (3) and which is guided in an axially displaceable manner on a carrier part (5) assigned to the closure element (2) in order to execute a lifting motion for the delivery of medium and can be locked with the aid of manually actuable spring bars (12) in at least one blocking setting, wherein the spring bars (12) are configured on an actuating plate (16) configured on the
(Continued)

Figure 11:
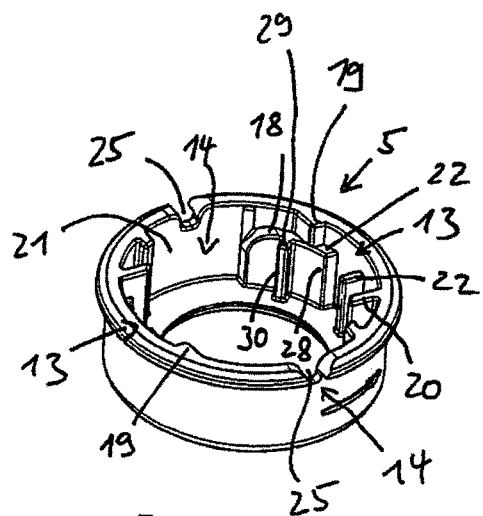

discharge portion (4), and respectively have an inner tongue, which can be bent radially inwards and to which, on an inner wall of the carrier part (5), is respectively assigned a guide ramp as an entry curve to a contact area, bounded by radial latches, of the blocking setting upon a rotary motion of the discharge portion (4).

8 Claims, 4 Drawing Sheets

(51) Int. Cl.
*A61M 31/00* (2006.01)
*A61F 9/00* (2006.01)

(52) U.S. Cl.
CPC ......... *B05B 11/3077* (2013.01); *A61F 9/0008* (2013.01); *A61M 15/08* (2013.01); *A61M 31/00* (2013.01); *A61M 2202/0007* (2013.01); *A61M 2205/276* (2013.01); *A61M 2210/0612* (2013.01); *A61M 2210/0618* (2013.01)

(58) Field of Classification Search
CPC ......... A61F 9/00; A61J 1/1443; A61J 1/1412; A61J 1/00; B05B 11/00; B65D 50/041; B65D 50/045; B65D 50/046
See application file for complete search history.

(56) References Cited

U.S. PATENT DOCUMENTS

| | | | |
|---|---|---|---|
| 4,991,746 A | | 2/1991 | Schultz |
| 5,232,687 A | * | 8/1993 | Geimer ................. A61F 9/0008 |
| | | | 424/400 |
| 6,065,648 A | * | 5/2000 | Tauber ................. B65D 47/242 |
| | | | 222/153.14 |
| 7,854,351 B2 | | 12/2010 | Bougamont |
| 2010/0292673 A1 | * | 11/2010 | Korogi ................. A61M 39/165 |
| | | | 604/533 |
| 2011/0094990 A1 | * | 4/2011 | Sprishen ............. B65D 50/041 |
| | | | 215/217 |

FOREIGN PATENT DOCUMENTS

| | | |
|---|---|---|
| JP | 2002320885 A | 11/2002 |
| WO | WO 2010/121264 A1 | 10/2010 |

OTHER PUBLICATIONS

International Search Report corresponding to PCT/EP2013/003818 dated May 2, 2014, two pages.

\* cited by examiner

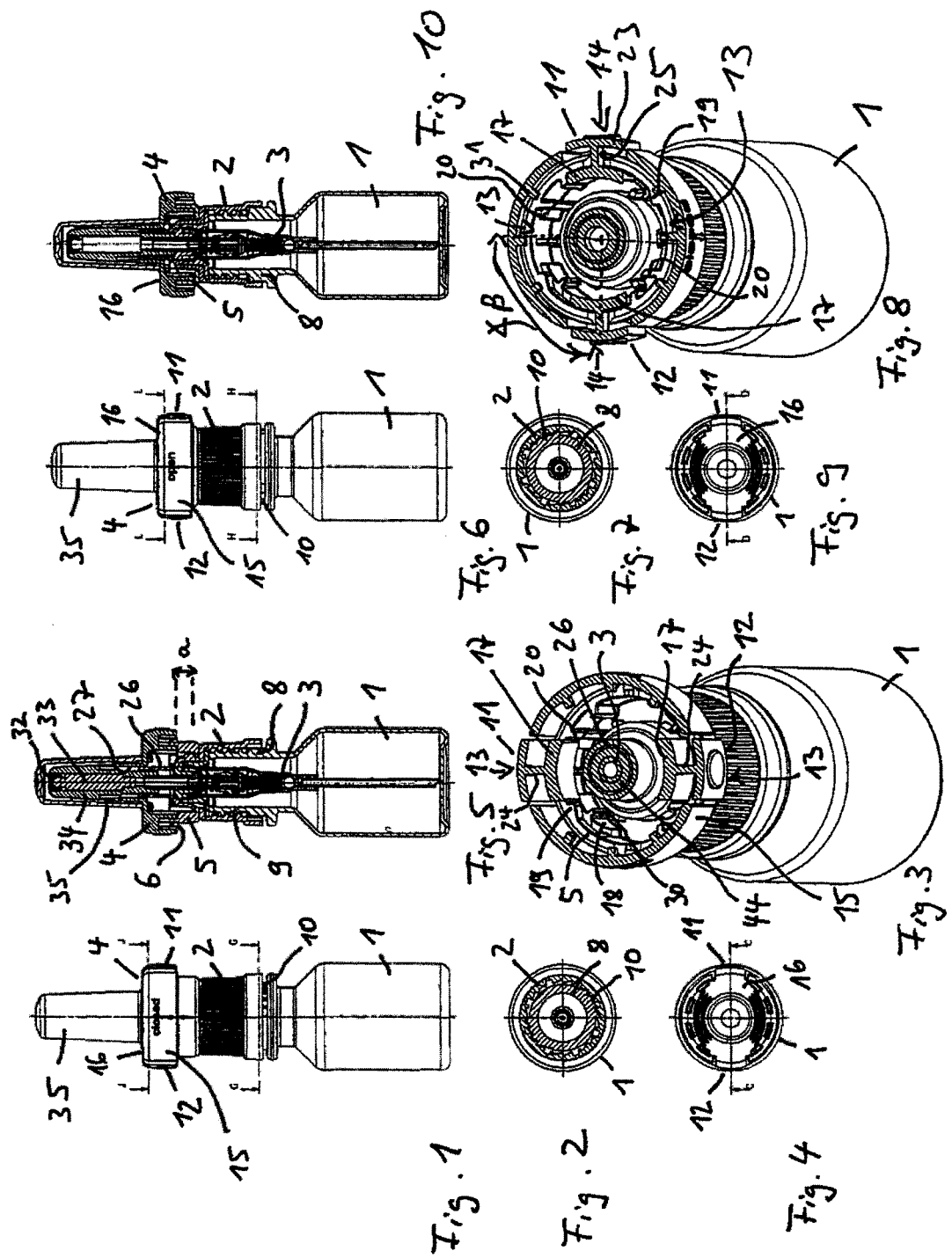

CHILD-PROOF DISCHARGER

The invention relates to a child-proof discharger for media according to the preamble to claim 1.

The invention relates to a child-proof discharger which is intended to prevent children from coming into contact with the content of a discharger. Opening mechanisms which are insurmountable by children are therefore provided. For some media, national and international laws even make the use of child-proof locks mandatory.

DE 101 34 796 A1 discloses a discharger for a medium according to the preamble to claim 1, which discharger prevents unauthorized access to the content of the medium in a reservoir, in particular for children. On the one hand, unauthorized actuation of a dosing head is precluded due to a manually releasable locking means. On the other hand, unauthorized removal of the entire discharger from the reservoir is also prevented, since a reservoir closure part is blocked by a locking mechanism.

DE 698 03 036 T2 discloses a discharger for a medium, which discharger comprises a closure device for an outlet region of a storage vessel for the medium. The closure device has a sleeve-like and internally threaded closure part, which can be screwed onto an external thread of the neck-shaped outlet region of the storage vessel. In order to prevent the closure device from being unscrewed again from the outlet region of the storage vessel and thus obtain a locking mechanism for the screwed-on discharger and for the medium content of the storage vessel, the closure part is surrounded by a cap-like locking part. The aim is thereby to prevent unauthorized access to the content of the storage vessel by simple unscrewing of the closure device.

A drawback is that the locking of a manually actuable pump part by means of the known spring bars is not sufficiently reliable.

The object of the invention is therefore to provide a child-proof discharger for media, in which unauthorized access to the content of the reservoir is better prevented.

This object is achieved by the features of claim 1.

A child-proof discharger in which the function of spring bars is combined with a rotary motion for moving the discharger in and out of a blocking setting is hereby provided. Such a combined motion, comprising a pressure component and a rotational component, produces a complex opening mechanism which can be regarded as child-proof.

According to the invention, the spring bars can be configured with a selectable width and faced with a finger pad. The pressure force which is necessary to release the spring bars from a blocking setting is also adjustable.

Further embodiments of the invention can be gleaned from the following description and the sub-claims.

Figure 13:
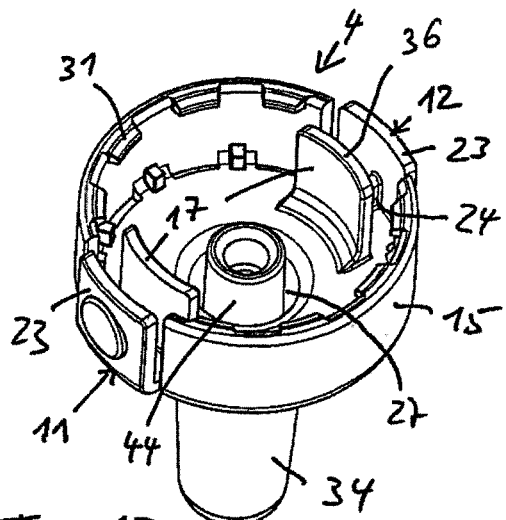
Figure 12:
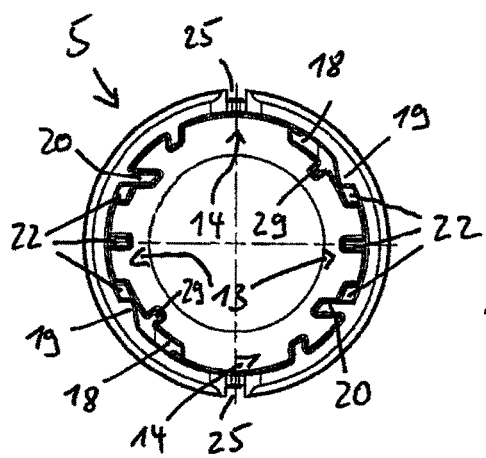
Figure 14:
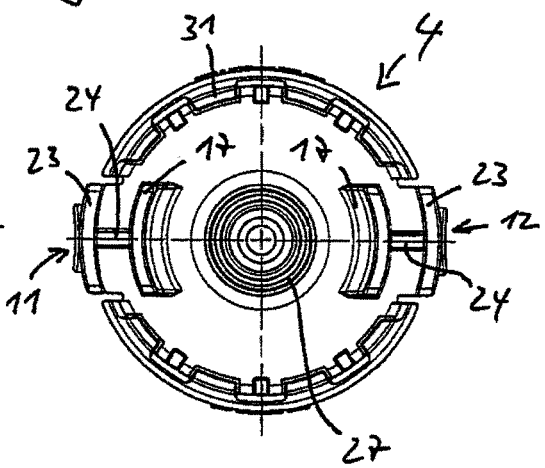
Figure 15:
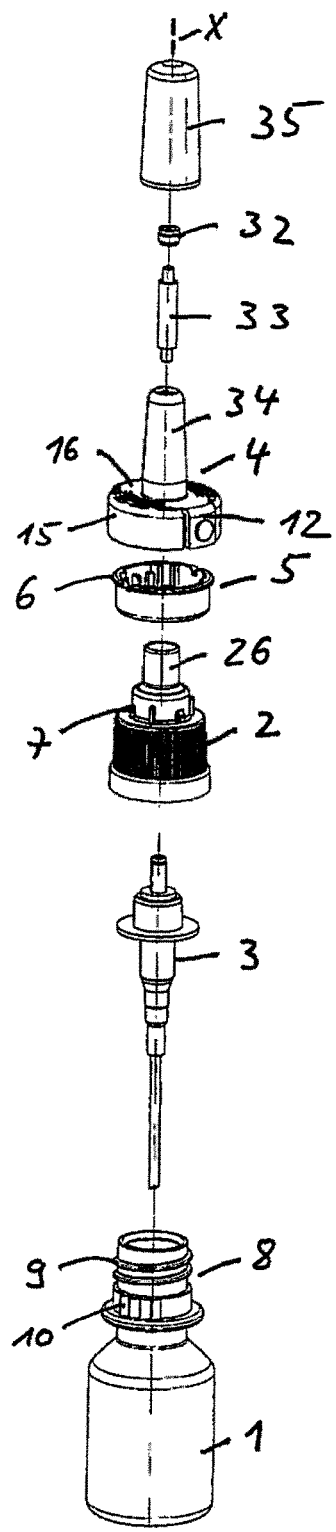
Figure 16:
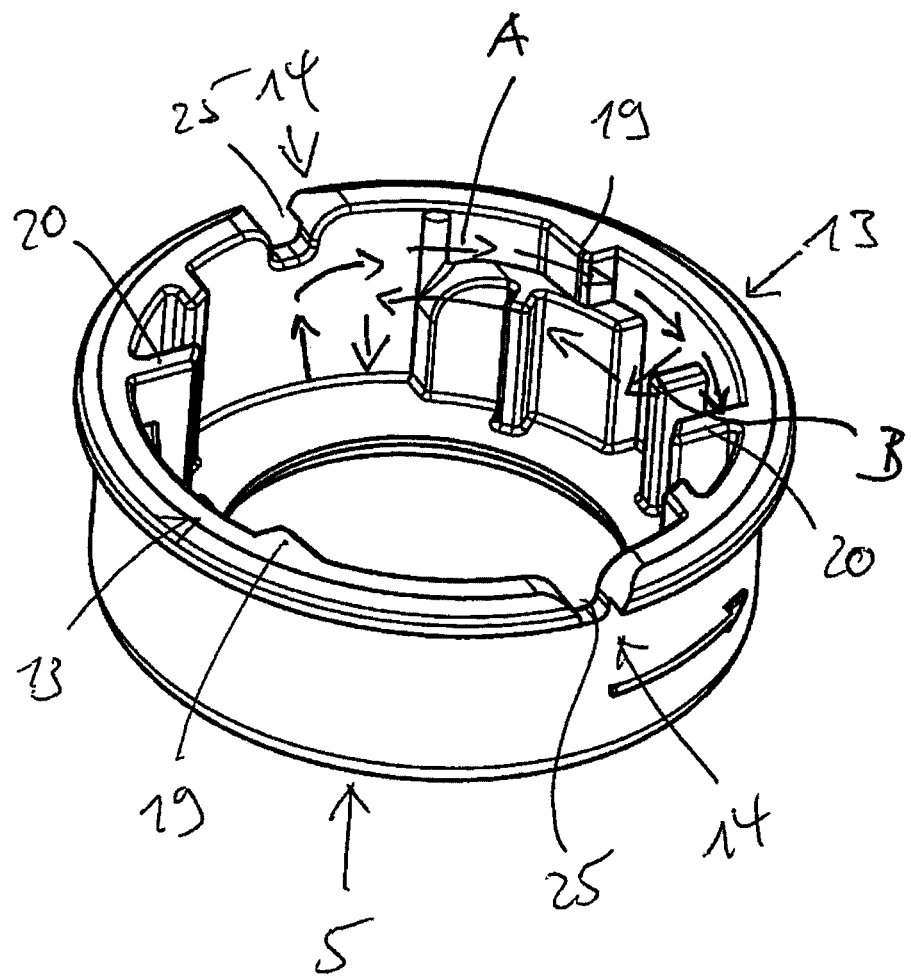

The invention is explained in greater detail below with reference to the illustrative embodiments represented in the appended figures, wherein:

FIG. 1 shows schematically a side view of a child-proof discharger in an upper rest position and locked in a "closed" blocking setting, FIG. 2 shows schematically a section G-G of FIG. 1, FIG. 3 shows schematically a section J-J of FIG. 1, FIG. 4 shows schematically a top view of FIG. 1, FIG. 5 shows schematically a section C-C of FIG. 4, FIG. 6 shows schematically a side view of a child-proof discharger in a lower actuating position and unlocked for an "open" actuating operation, FIG. 7 shows schematically a section H-H of FIG. 6, FIG. 8 shows schematically a section K-K of FIG. 1, FIG. 9 shows schematically a top view of FIG. 6, FIG. 10 shows schematically a section D-D of FIG. 9, FIG. 11 shows schematically a perspective view of the carrier part, FIG. 12 shows schematically a top view of the carrier part, FIG. 13 shows schematically a bottom view of a discharge portion positioned upside-down, FIG. 14 shows schematically a top view of FIG. 13, FIG. 15 shows schematically an exploded representation of the child-proof discharger, FIG. 16 shows schematically a path of motion of an inner tongue on the inner marginal region of a carrier part.

The invention relates to a child-proof discharger for media, comprising a reservoir 1 and a pump part 3, mounted on the, reservoir 1 in sealed arrangement via a closure element 2, for pumping medium out of the reservoir 1. Mounted on the pump part 3 is an actuable discharge portion 4, which is guided in an axially displaceable manner on a carrier part 5 assigned to the closure element 2 in order to execute a lifting motion for the delivery of medium. The discharge portion 4 is movable, for actuation of the pump part 3, by an actuation path a between a lower actuating position according to FIG. 10 and an upper rest position according to FIG. 5. In addition, the discharge portion 4 is rotatable in relation to the carrier part 5 about a centre axis X. For the execution of the translatory motion, preferably axially in the X-direction, and for the execution of the rotary motion of the discharge portion 4 in relation to the carrier part 5, the discharge portion 4 is fixed to the carrier part 5, preferably via a snap connection 6. The carrier part 5 itself is fixed to the closure element 2 by a fastening device 7 in order that the carrier part 5 assumes a preferably fixed position in relation to the reservoir neck 8. The carrier part 5 and the closure element 2 can also be configured in one piece.

The closure element 2 can be provided in a known manner with an internal thread, which can be screwed onto an external thread 9 on the reservoir neck 8. A barbed toothing 10 can secure this screw connection and prevent unscrewing. Alternatives to the screw closure are, for instance, flange closures or snap closures. The closure element 2 surrounds the reservoir neck 8 preferably in a sleeve-like manner, which makes it more difficult to pull off the reservoir neck 8.

The shape of the discharge portion 4 can be chosen according to the purpose of use. According to FIG. 1 to FIG. 15, the discharge portion 4 is configured in the shape of a connecting piece for nasal application. For the dispensing of eye drops, the discharge portion 4 is preferably configured with a shorter connecting piece shape than that which is represented.

For the locking of the discharge portion 4 in the upper rest position, as is represented in FIG. 1 to FIG. 5, the discharge connecting piece 4 can be locked with the aid of manually actuable spring bars 11, 12 in at least one blocking setting 13 on the carrier part 5 in order to prevent unauthorized access to the content of the reservoir 1. In the blocking setting 13, the discharge portion 4 cannot be moved into the lower actuating position. This is only possible if the spring bars 11, 12 are positioned in an actuating setting 14 relative to the carrier part 5.

The spring bars 11, 12 are configured on a casing ring 15, configured on the discharge portion 4, of an actuating plate 16, and are preferably two oppositely situated spring bars 11, 12. Each spring bar 11, 12 respectively has an inner tongue 17, which can be bent by manual action radially inwards and to which, on an inner wall 21 of the carrier part 5, is respectively assigned a peripherally extending guide ramp 18 as an entry curve to a contact area 22, bounded by radial latches 19, 20, as a blocking setting 13 upon rotation of the discharge portion 4 about the centre axis X.

The contact area 22 preferably has a height at which the inner tongue 17, by bearing contact against the contact area 22, holds the discharge portion 4 in the upper rest position.

The spring bars 11, 12 respectively have an inner tongue 17 and an outer tongue 23, which are radially spaced and are preferably arranged parallel to each other. Between the respectively inner tongue 17 and outer tongue 23 is arranged a wall 24 for a connecting-link-type guidance of the discharge portion 4 on the carrier part 5, for which purpose the said wall has a slot 25 in the lifting direction of the centre axis X.

The closure element 2 preferably has an axially extending pin 26, which penetrates the here sleeve-like carrier part 5 and reaches into an axial guideway 27 of the discharge portion 4 for the axial mounting of the discharge portion 4 on the closure element 2 upon the lifting motion for discharge of a medium and upon the rotation into the blocking setting 13. Tilting of the discharge portion 4, which could make it easier to release the blocking setting 13, is thereby avoided.

The guide ramp 18 can define a section in the peripheral direction of the preferably round carrier part 5, which section determines a twist angle (3 of the discharge portion 4 in relation to the carrier part 5 into the blocking setting 13. The guide ramp 18 also preferably has an end portion 28, which extends into the contact area 22. This end portion 28 thus forms a transfer portion, which, via the inlet-side latch 19, guides the respectively inner tongue 17 into the blocking setting 13. Thus a transport into the blocking setting 13 via a sliding surface of the transfer portion is further improved.

The contact area 22 can be configured as a multi-material support, which is advantageous, in particular, from a production engineering aspect.

For a motion of the inner tongue 17 past the radial inlet-side latch 19, the guide ramp 18 can also have a surface widening 29. The inner tongue 17, and thus the discharge portion 4, is thereby reliably held in the upper rest position during the rotation of the discharge portion 4, since the inner tongue 17 is reliably prevented from sliding off the guide ramp 18.

The surface widening 29 can be formed, for instance, by an end face of a rib 30.

The actuating plate 16 of the discharge portion 4 can have a casing ring 15 which can be snapped onto the carrier part 5, for which purpose latch bosses 31 are arranged distributed over the periphery.

The spring bars 11, 12 are preferably formed by axial wall portions of the casing ring 15 and are selectable in width and thickness.

The above statements in relation to one spring bar 11, 12 apply equally to the respectively other spring bar 11, 12.

The working method of the child-proof lock is as follows. By rotation of the discharge portion 4 in the upper rest setting, the respectively inner tongue 17 can latch via the respective guide ramp 18 into the blocking setting 13. In the upper rest setting, the discharge portion 4 is held via a restoring spring of the pump part 5. From this blocking setting 13 which locks the discharge portion 4, the inner tongues 17 can only be unlatched by compression of the two spring bars 11, 12. Under the effect of this pressure motion, the discharge portion 4 can be turned back until the respectively inner tongue 17 makes its way into the actuating setting 14, where a lifting motion of the discharge portion 4 is again possible. Preferably, a free end 36 of the respectively inner tongue 17 enters into sliding contact with the guide ramp 18 when the discharge portion 4 and the carrier part 5 are twisted relative to each other, to be precise starting from the upper rest setting, as represented in FIG. 5. The motional path A of an inner tongue 17 from the actuating setting 14 into the blocking setting 13 is in FIG. 16 represented schematically on the basis of motion arrows. For the release of the tongue 17 from the blocking setting 13, the resistance of the latch 19 must be surmounted, which makes it necessary for the spring bars 11, 12 to be compressed. The respective tongue 17 is thereby subjected to an inwardly directed motional component B. This enables the respective tongue 17 to be moved back into the actuating setting 14.

As FIG. 15 shows, a nozzle insert 32 and a fluid path insert 33 can finally be inserted in known manner into the discharge portion 4. Lastly, for the protection of a connecting piece 34 of the discharge portion 4, a protective cap 35 can be removably mounted. As FIG. 13 shows, the discharge portion 4 can have a connector 44 for the connection of the pump part 3.

Instead of two opposing spring bars 11, 12, a greater number of spring bars, which are arranged distributed over the periphery, can also be provided.

The invention claimed is:

1. Child-proof discharger for media, comprising:
   a reservoir (1),
   a pump part (3), mounted on the reservoir (1) in sealed arrangement via a closure element (2), for pumping medium out of the reservoir (1), and
   an actuable discharge portion (4) having
      an actuating plate (16) and a casing ring (15) extending downward therefrom,
      wherein the discharge portion (4) is mounted on the pump part (3), such that the casing ring is snapped onto a carrier part (5), an is guided in an axially displaceable manner on a carrier part (5) disposed on the closure element (2) in order to execute a lifting motion for the delivery of medium and which can be locked with the aid of manually actuable spring bars (11, 12) in at least one blocking setting (13),
      wherein the spring bars (11, 12) are configured and disposed circumferentially in-line with, between, and separated from the casing ring (15),
   wherein the actuating plate (16) is disposed on the discharge portion (4) and each spring bar (11, 12) includes an outer tongue (23) and an inner tongue (17) each connected together via a link, and further wherein the spring bars (11, 12) can each be bent radially inwards relative to an inner wall (21) of the carrier part (5),
   wherein each of the respective spring bars (11, 12) is respectively assigned a guide ramp (18) as an entry curve to a contact area (22) that is bounded by radial latches (19, 20) of the at least one blocking setting (13) upon a rotary motion of the discharge portion (4),
   wherein the respective inner tongues (17) are disposed radially inward of the entirety of the casing ring (15), and
   wherein the spring bars (11, 12) are configured to be bent only when respective links of the spring bars (11, 12) are disposed in a respective slot (25) of the carrier part (5).

2. Child-proof discharger according to claim 1, characterized in that the closure element (2) has a pin (26), which extends axially through the carrier part (5) and which reaches into an axial guideway (27) of the discharge portion (4) for the axial mounting of the discharge portion (4) on the closure element (2).

3. Child-proof discharger according to claim 1, characterized in that the guide ramp (18) defines a section which determines a twist angle (13) of the discharge portion (4) in relation to the carrier part (5) into the blocking setting (13).

4. Child-proof discharger according to claim 1, characterized in that the guide ramp (18) has an end portion (28), which extends into the contact area (22).

5. Child-proof discharger according to claim 1, characterized in that, for a motion of the respectively inner tongue (17) over a radial latch (19), the guide ramp (18) has a surface widening (29).

6. Child-proof discharger according to claim 5, characterized in that the surface widening (29) is formed by an end face of a rib (30).

7. Child-proof discharger according to claim 1, characterized in that the closure element (2) can be screwed, flanged or snapped onto a reservoir neck (8) of the reservoir (1).

8. Child-proof discharger according to claim 7, characterized in that the closure element (2) surrounds the reservoir neck (8) in a sleeve-like manner.

* * * * *